United States Patent [19]

Tahvonen et al.

[11] Patent Number: 5,811,090
[45] Date of Patent: Sep. 22, 1998

[54] MICROORGANISMS FOR BIOLOGICAL CONTROL OF FUNGAL INFECTIONS AND PESTS OF PLANTS

[75] Inventors: Risto Tapio Tahvonen, Jokioinen; Milja Tuulikki Keskinen, Vantaa; Marja-Leena Lahdenperä, Helsinki; Pekka Tapani Seiskari, Kirkkonummi; Esa Petri Teperi, Hämeenlinna; Ulla Anita Tuominen, Espoo, all of Finland

[73] Assignee: Kemira Agro Oy, Helsinki, Finland

[21] Appl. No.: 682,624

[22] PCT Filed: Jan. 27, 1995

[86] PCT No.: PCT/FI95/00042

§ 371 Date: Sep. 23, 1996

§ 102(e) Date: Sep. 23, 1996

[87] PCT Pub. No.: WO95/20646

PCT Pub. Date: Aug. 3, 1995

[30] Foreign Application Priority Data

Jan. 31, 1994 [FI] Finland .................................. 940463

[51] Int. Cl.⁶ .......................... A01N 63/00; A01N 25/00; C12N 11/00; C12N 11/16
[52] U.S. Cl. .......................... 424/93.5; 424/405; 424/409; 435/174; 435/260; 435/267; 435/911; 435/254.1
[58] Field of Search .................................. 424/93.5, 405, 424/409; 435/243, 254.1, 254.2, 174, 260, 267, 911

[56] References Cited

U.S. PATENT DOCUMENTS

| | | | |
|---|---|---|---|
| 4,647,533 | 3/1987 | Weller et al. | 435/29 |
| 4,748,021 | 5/1988 | Chet et al. | 424/93 |
| 4,818,530 | 4/1989 | Marois et al. | 424/93 |
| 4,996,157 | 2/1991 | Smith et al. | 435/254 |
| 5,260,302 | 11/1993 | Fattori et al. | 435/34 |

FOREIGN PATENT DOCUMENTS

| | | |
|---|---|---|
| 228457 | 7/1987 | European Pat. Off. . |
| WO 90/01327 | 2/1990 | WIPO . |
| WO 92/18613 | 10/1992 | WIPO . |

*Primary Examiner*—David M. Naff
*Assistant Examiner*—Deborah K. Ware
*Attorney, Agent, or Firm*—Marshall, O'Toole, Gerstein, Murray & Borun

[57] ABSTRACT

The present invention relates to biological control of plant diseases and concerns new microorganisms belonging to the genus Nectria, as well as their use for controlling fungal infections in plants. The invention also concerns compositions comprising new strains of the genus Nectria and their use for these purposes. The invention also provides a method of screening effective control organisms from microbial strains isolated from soil.

23 Claims, 3 Drawing Sheets

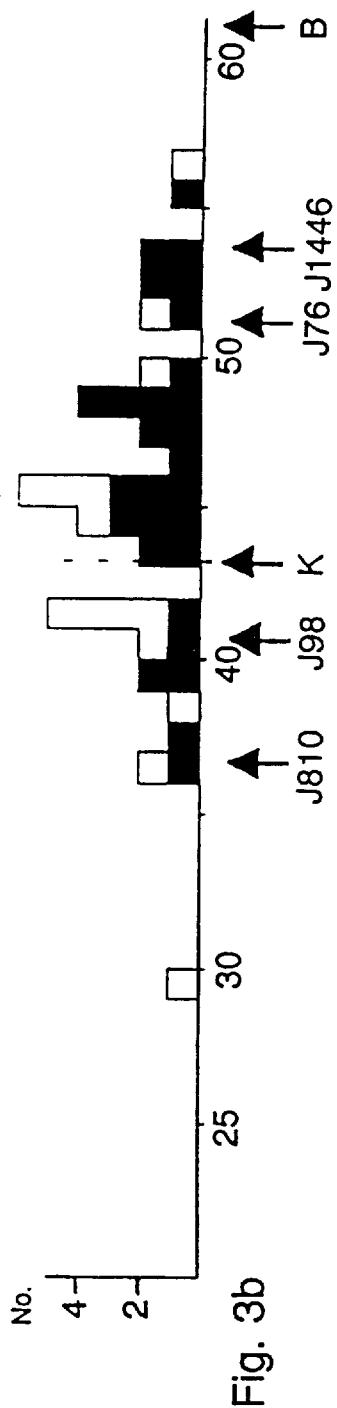
Fig. 3a
Fig. 3b

□ = one isolate isolated from roots   ■ = one isolate isolated directly from soil

MICROORGANISMS FOR BIOLOGICAL CONTROL OF FUNGAL INFECTIONS AND PESTS OF PLANTS

FIELD OF THE INVENTION

The present invention relates to biological control of plant diseases and concerns specifically new microorganisms belonging to the genus Nectria, as well as their use for controlling fungal infections in plants. The invention concerns also compositions comprising new strains of the genus Nectria and their use to said purpose. The invention provides also a method for screening effective control organisms from microbial strains isolated from soil.

BACKGROUND OF THE INVENTION

Agricultural crops are afflicted with various fungal, bacterial and viral diseases as well as a number of insect pests. Many cultivation technical, chemical and biological control methods have been developed in order to control these. The purpose of such methods is to prevent the qualitative and quantitative crop losses caused by plant diseases and other pests.

In general the term biological control of plant diseases means the control of plant pathogens by other organisms, which can be called biological control agents (BCA). Products developed of BCA's are often called biopesticides. The mechanisms of the biological control of plant diseases do vary, and the effect is often based on the cooperative action of many different mechanisms. The control effect may be based on inhibitory metabolites produced by the control agent, sometimes it can parasitize the pathogen or compete with it for space and/or nutrients available.

The need of discovering new biological control agents has been increased by the fact that many of the traditional chemical control agents has turned out to be deleterious to the environment and human beings. A disadvantage of the chemicals is also the fact that many pests have become resistant to one or even a number of control agents. The development of resistance to biopesticides is instead improbable because the effect thereof is based on a number of mechanisms of different types. The chemicals usually effect faster and more effectively than biopesticides. Biopesticides for their part are often longer-acting than chemicals as their effect is based on a viable and reproducible microorganism.

The most important group of biopesticides are bacterial products directed against insects. Bioinsecticides based on the bacterium *Bacillus thuringiensis* are the most commonly used. A biofungicide based on the actinomycete Streptomyces being effective against a number of soil-borne and seed-borne fungal diseases of plants is produced in Finland. A product which is able to prevent the spreading of Fomes root rot (caused by *Heterobasidion annosum*) in coniferous forests has been developed from a harmless wood rotting fungus *Phlebia gigantea*.

Bacteria of the genus Pseudomonas, especially of the species *Pseudomonas fluorescens* have been studied a lot and nowadays a great amount of *P. fluorescens* strains are known which have fungicidic activity. See e.g. published patent applications WO 92/18613, FI 92 1722 and WO 90/01327, as well as EP-patent 228 457.

While searching microorganisms suitable for biological control great amounts of microbial strains are usually screened for control activity or another certain property. Some screening methods have been described in patent publications.

In U.S. Pat. No. 4,647,533 a three-step screening method is described where bacteria are first isolated from soil which contains plenty of spores of the deleterious fungus Pythium. In the second step the isolated bacteria are screened in a greenhouse by growing cereal seeds in soil containing a great amount of Pythium spores with suspension of each bacterium to be tested and (the control test) without it, and from this test those bacteria are selected in the presence of which the plants develop biggest leaves and grow also otherwise tallest. In the third step the selected bacteria are further selected in field in a similar test than the greenhouse test. Also at this step those bacteria are selected in the presence of which the plants grow best.

In the FI patent application No. 92 1722 on the other hand the following process is used. First the mycelia of a Pythium strain is grown on a suitable growth medium, on the mycelia a layer of sterile soil is set, to which the microorganism to be tested is added, and its effect on the growth of Pythium is evaluated. At the second stage a soil sample is inoculated by a Pythium strain causing damping-off, a seed of a plant sensible to the fungal infection is sown in soil and the effect of the test organism on plant growth is determined. To the further tests those substances are selected which are inhibitory to Pythium in both of the above mentioned tests.

SUMMARY OF THE INVENTION

The present invention relates to a microorganism of the genus Nectria, i.e. *Nectria pityrodes* Montagne, which was found to be very active especially against Fusarium fungi.

The invention relates further to a biofungicidal composition prepared of the microbial strain which comprises as an active ingredient the above mentioned fungal strains belonging to the genus Nectria and optionally additives or carriers conventional in the art as an appropriate formulation. Examples of such formulations are compositions suitable for seed dressing, powdered or granular compositions to be spread on growth substrates or liquid formulations to treat the soil.

The present invention also provides a new and efficient screening procedure of fungal strains, in which a three-step test sequence is used, comprising a sand, peat and field soil test. In each test step the fungal strains which appear to be inefficient are eliminated from further tests. The fungal strains shown to be the very best in the greenhouse are then brought to the screening tests in field conditions.

Figure 1:
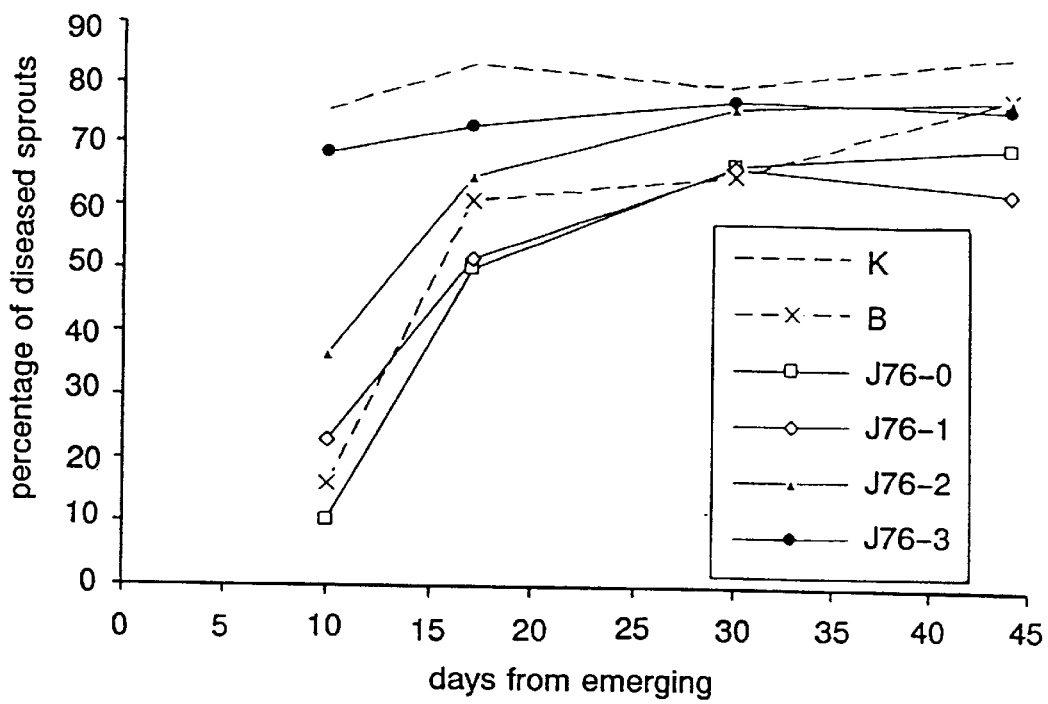
FIG. 1. The dose response experiment with J76 in the summer -92. The percentage of diseased sprouts using seed inoculated with the fungus *F. culmorum*.
Figure 2:
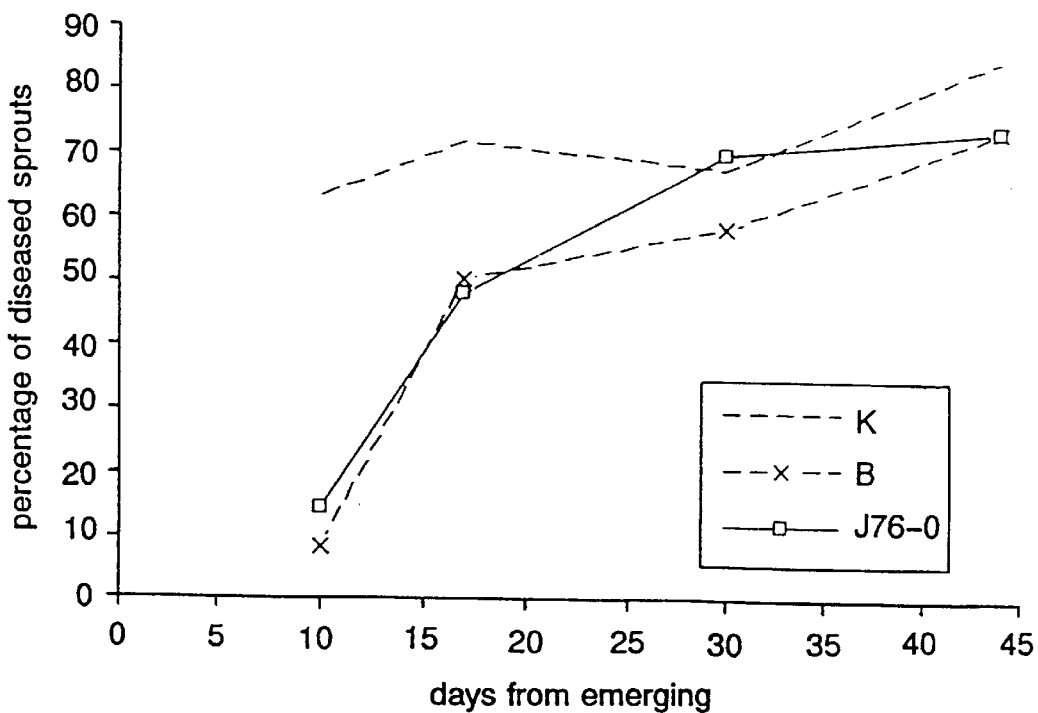
Figure 3C:
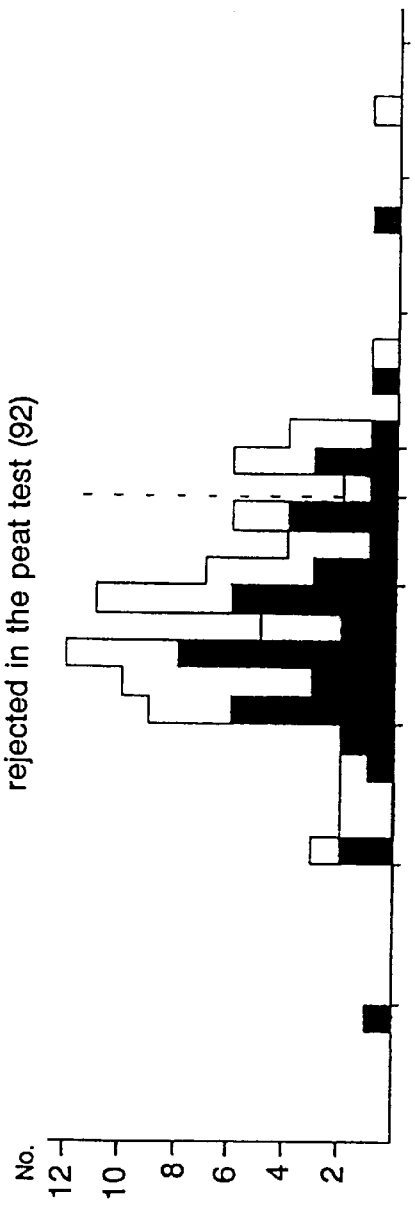
Figure 3D:
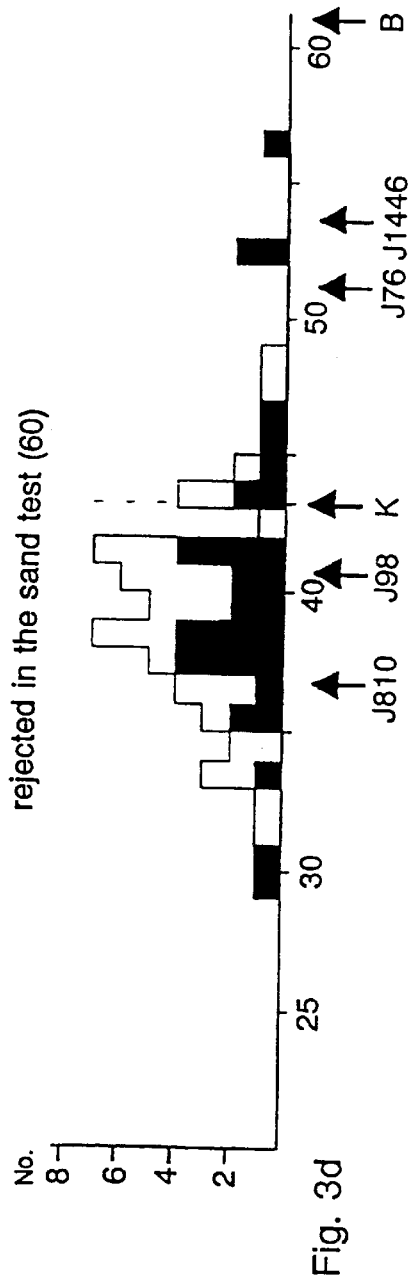

K=Not treated, B=Baytan dressing,
J76-0=spore suspension of J76, $1.2 \times 10^7$ cfu/ml
J76-1=spore suspension of J76, $1.2 \times 10^6$ cfu/ml
J76-2=spore suspension of J76, $1.2 \times 10^5$ cfu/ml
J76-3=spore suspension of J76, $1.2 \times 10^4$ cfu/ml FIG. 2. The dose response experiment with J76 in the summer -92. The percentage of diseased sprouts when using healthy seed. The abbreviations as in FIG. 1.

FIGS. 3a to 3d. Histograms representing the effect of the fungal isolates rejected at the different stages of the greenhouse tests on the health of the sprouts in field conditions. K=Not treated, B=Baytan I dressing.

DETAILED DESCRIPTION OF THE INVENTION

Below the fungal strains of the invention are described in detail. Their isolation and characterization, and testing of their effectiveness in field conditions are reported. Further are described the formulation of the biofungicidal compositions formed of these strains, the characteristics of the compositions and effectiveness tests with these compositions. A method for screening the fungal strains isolated from soil samples is also described.

Isolation of the Microorganisms

The soil samples, from where the fungal strains of the invention have been isolated, were collected in years -89, -90 and -91, alltogether about 190. The samples were collected from different parts of Finland, mainly from the research stations of MTT (Agricultural Research Centre), from different soil types and different crop rotations. The samples were taken from the root layer (0–15 cm depth). Several subsamples were taken from each field, which were pooled to samples of 1 to 2 liters.

The isolations were made either by a dilution method (soil isolations) or a bait plant method (root isolations), the performance of which are described in detail hereinafter in the section Methods.

Characterization of the Microorganisms

The fungal strains isolated from the soil samples were tested with the screening method of the invention, which is described hereinafter in the section Methods. Then five strains were found, which gave very good results. The strains, which were named J76, J1431, J1432, MOS1 and ROS2, where characterized at Centraalbureau voor Schimmelcultures, Baarn, Netherlands. These strains have been deposited according to the Budapest Treaty to the DSM depository (Deutsche Sammlung von Mikroorganismen und Zellkulturen GmbH) by deposit numbers DSM 7522 (Mar. 15, 1993), DSM 8805 (Dec. 10, 1993), DSM 8806 (Dec. 10, 1993), DSM 8807 (Dec. 10, 1993) and DSM 8808 (Dec. 10, 1993), respectively.

The morphological characteristics of the microorganisms are the following:

Morphology: Sporodochia without marginal sterile hyphae. Conidiophores branched repeatedly, with several branches arising at each node. Ultimate branches bear whorls of phialides arranged in a palisade-like layer. Phialides cylindric, up to 15 $\mu$m long, with an apical pore. Conidia produced in chains or slimy balls, ellipsoidal to droplike with a short hilum, 7–8×4 $\mu$m, smooth-walled, without appendage.

Colony habit: Colony on oatflake-agar growing to a diameter of 40 mm at 22° C. in 7 days; mycelium hyaline, sporulating areas pustulate sporodochial, green, arranged in concentric rings. Odour not prominent, colony reverse colourless, exudate limited, clear.

The conidiophore structure of J76 strain is similar to that of *Myrothecium verrucaria,* but it differs from this species by the production of non-marginate sporodochia, conidia in dry chains and without the typical fan-like appendage.

The representatives of the genus Gliocladium differ from the new strains in that it is typical for Gliocladium to produce individual penicillate conidiophores.

The strains J76, J1431, J1432, MOS1 and ROS2 were thus identified as the species *Nectria pityrodes* Montagne.

From these strains non-perishable formulations can be prepared, which are easy to spread onto plantations which require disease control. A formulation can be produced e.g. in the form of powder. Cultivation of a microbe can be started from an inoculum, which is a PDA pellet including spores, and which has been kept at −80° C. The microbe can be cultivated either as a liquid culture or on a solid support. The nutrient medium comprises sugar, e.g. sucrose, and nitrogen as well as small amounts of other nutrients. In the cultivations non-specific nutrient media can be used, e.g. Corn Steep Liquor (CSL), or specific nutrient media, e.g. GYM (glucose 4 g/l, yeast extract 4 g/l, malt extract 10 g/l) or PDB (potato-dextrose-broth). pH is about 6.0, it is adjusted in the beginning before sterilization. The cultivation is performed shaking from one week to two weeks. The cell mass can be separated from the broth either by filtering through filter paper or by centrifuging. If liquid cultivation is used, to the cell mass a carrier is mixed, e.g. silica, milk powder and/or CMC (carboxymethylcellulose). The mass is dried at room temperature and milled to powder.

Methods

Isolations of the microbes:

a) Dilution method (soil isolations)

10 g of soil was mixed to 100 ml of 0.5% water agar (Bacto-agar). Three 10 ml subsamples were taken from the mixture and from each of them two dilutions ($10^{-1}$ and $10^{-2}$) were made into 0.5% water agar. The dilutions were shaken (in water bath) in a shaker from 20 to 30 min. 1 ml of the dilution was pipetted on an empty petri dish and 20 ml of Littman Oxgall Agar (LOA) was poured on. The dishes were incubated at room temperature for 3–7 days and individual fungi were then isolated into pure cultures on PDA (Potato Dextrose Agar).

b) Bait plant method (root isolations)

15 pots in a serial pot plate (Vefi-VP 96 serial pot plate with 50 ml pots) were filled with soil from one sample. Four seeds of wheat, four of barley or about 15 of turnip rape were sown into one pot and five pots were used for each of the plant species. The seeds were covered with sand and the pots were watered and incubated in a growth chamber at +15° C. with a 14 h daylength. After two weeks of cultivation the plants were picked up and washed in running water or cleaned up with a brush without water. From the roots small pieces were cut and they were put on plates. The media used: LOA (10 g peptone, 10 g dextrose, 15 g Bacto-Oxgall, 0.01 g B-chrystal violet, 0.03 g streptomycin, 20 g agar, ad. 1000 ml water), PCNB (15 g peptone, 1 g $KH_2PO_4$, 0.5 g $MgSO_4.7H_2O$, 2 g Avicol, 3 ppm streptomycin, 20 g agar, ad. 1000 ml water) and PDA-Streptomycin (39 g PDA-preparation, 300 ppm streptomycin, ad. 1000 ml water). After a few days of incubation single fungi were isolated and subcultured onto PDA plates.

The strains were stored on PDA pellets in ampoules (Nalgene 5000-0012, PP Sterile 1.2 ml) at −80° C.

Performance of the Green House Tests of the Screening Method

Sand test

Seeds of a cereal are sown on a sand layer. First mycelia and spores of the pathogen and then spores of the test fungus are pipetted in a water suspension on the seeds and to the growth substrate, whereafter the seeds are covered by sand. After two and a half weeks the intensity of the disease symptoms of the sprouts are examined. From further experiments those fungi are rejected which do not affect the intensity of the disease or which prove to be pathogenic themselves.

Peat test

A seed of a cereal is wetted in a spore suspension of a pathogen, and dried. After this the seed is wetted with the spore suspension of the test fungus, dried and sown. Steamed peat is used as growth substrate. After two and a half weeks of cultivation observations on the health of the sprouts are made. Fungal strains which clearly prevent the disease, are taken to the field soil test.

Field soil tests

Grounded and wetted field soil is put in 1.5 l pots and 36 cereal seeds are sown into each pot. The seed treatments before sowing are made as in the peat test, and three replicate pots are used for each treatment. The symptoms of the sprouts are examined after four weeks of cultivation.

Strains which are found good in these tests are taken to the field tests, which give the final certainty of the biopesticidal effect of the microbial isolates selected.

Pathogenicity of the Fungal Strains

Possible detrimental effects of the J76 fungal strain have been tentatively examined. Results got so far show that the fungus is not pathogenic to plants. There were 33 plant species tested.

EXPERIMENTAL

The following experiments illustrate the utilization of the invention. In item (A) the use of spore suspensions of Nectria pityrodes strains J76, J1431, J1432, MOS1 and ROS2 of the invention, for controlling plant diseases caused mainly by Fusarium spp. is described. In item (B) the preparation and use of the formulations made from these strains are described, in item (C) the experiments are described, by which the mode of action by the J76 fungal strain was examined, and in item (D) the performance and evaluating of the screening method of the invention is described.

(A) Use of the Fungal Strains as Spore Suspensions

Experiments with Spore Suspension of the Strain J76

In the summer -92 the effect of the spore suspension of the strain J76 was examined in three test places. In the tests two different seeds were used: wheat artificially inoculated with Fusarium culmorum and barley naturally infected by F. nivale.

The results of wheat tests are given in Table 1. The yield results by artificially inoculated wheat are given in Table 2.

The sprout observations with barley are given in Table 3. The disease had no statistically significant effect on the yield of barley.

TABLE 1

The three test place experiments in the summer -92 with artificially inoculated wheat. Emergence and disease rate of the sprouts.

| treatment | sprouts - number/ rowmeter | disease rate - percentage of severely diseased sprouts |
| --- | --- | --- |
| JOKIOINEN: | | |
| healthy seeds | 50 | 5.2 |
| untreated | 11 | 48 |
| Baytan-dressing | 45 | 10 |
| J76 | 47 | 7.2 |
| MIETOINEN: | | |
| healthy seeds | 45 | 7.3 |
| untreated | 10 | 42 |
| Baytan-dressing | 39 | 3.8 |

TABLE 1-continued

The three test place experiments in the summer -92 with artificially inoculated wheat. Emergence and disease rate of the sprouts.

| treatment | sprouts - number/ rowmeter | disease rate - percentage of severely diseased sprouts |
| --- | --- | --- |
| J76 | 33 | 13 |
| PÄLKÄNE: | | |
| healthy seeds | 50 | 3.0 |
| untreated | 15 | 57 |
| Baytan-dressing | 51 | 24 |
| J76 | 45 | 11 |

TABLE 2

The three test place experiment in the summer -92 with artificially inoculated wheat. Yield results (kg/ha).

| treatment | JOKIOINEN | MIETOINEN | PÄLKÄNE |
| --- | --- | --- | --- |
| healthy seeds | 3650 | 3190 | 5290 |
| untreated | 1830 | 1690 | 1950 |
| Baytan-dressing | 3270 | 3190 | 4940 |
| J76 | 3530 | 2950 | 4900 |

TABLE 3

The three test place experiment in the summer -92 with naturally infected (F. nivale) barley. Emergence and disease rate of sprouts.

| treatment | sprouts - number/ rowmeter | disease rate - percentage of severely diseased sprouts |
| --- | --- | --- |
| JOKIOINEN: | | |
| untreated | 39 | 7.7 |
| Baytan-dressing | 40 | 1.2 |
| J76 | 40 | 0.9 |
| MIETOINEN: | | |
| untreated | 42 | 7.4 |
| Baytan-dressing | 42 | 1.4 |
| J76 | 43 | 2.8 |
| PÄLKÄNE: | | |
| untreated | 42 | 26 |
| Baytan-dressing | 42 | 9.4 |
| J76 | 44 | 6.3 |

The Dose Response Test of the Strain J76 in the Summer -92

As J76 showed really good results in the sprout observations in the beginning of summer -92, the effect of its application rate on the control effect was tested in an experiment, which was sown just prior the midsummer. Both healthy wheat seed and seed artificially inoculated with Fusarium culmorum were used.

Small 2 m$^2$ plots were used in the experiment. Emergence and disease symptoms on the sprouts were observed. The sprout samples for the disease follow-up were collected at four different points of time. The samples for each treatment were taken from four plots sown separately for each sampling time. The observed amounts of the sprouts are given in Table 4 and the percentages of the diseased sprouts are given in Table 5 separately for diseased and healthy seed. The data of Table 5 are shown graphically in FIGS. 1 and 2.

TABLE 4

The dose response experiment for J76 in the summer -92. Emergence.

| treatment | sprouts number/rowmeter |
|---|---|
| Seeds infected with Fusarium | |
| Untreated | 18 |
| Baytan-dressing | 57 |
| J76 spore suspension ($1.2 \times 10^7$ cfu/ml) | 74 |
| J76 spore suspension ($1.2 \times 10^6$ cfu/ml) | 58 |
| J76 spore suspension ($1.2 \times 10^5$ cfu/ml) | 51 |
| J76 spore suspension ($1.2 \times 10^4$ cfu/ml) | 20 |
| Healthy seeds: | |
| Untreated | 71 |
| Baytan-dressing | 66 |
| J76 spore suspension ($1.2 \times 10^7$ cfu/ml) | 80 |

TABLE 5

The dose response experiment for J76 in the summer -92. Percentage of diseased sprouts with seed inoculated with *F. culmorum*, and healthy seed. Abbreviations as in FIG. 2.

| | days from emergence | | | |
|---|---|---|---|---|
| treatment | 10 | 17 | 30 | 44 |
| Fusarium-infected seed: | | | | |
| K | 75.4 | 82.8 | 79.5 | 85.1 |
| B | 15.9 | 60.9 | 65.3 | 78.2 |
| J76-0 | 10.1 | 50.0 | 66.6 | 70.3 |
| J76-1 | 23.1 | 51.8 | 55.5 | 62.9 |
| J76-2 | 36.4 | 64.7 | 76.0 | 78.0 |
| J76-3 | 68.6 | 72.8 | 77.1 | 76.2 |
| healthy seed: | | | | |
| K | 54.7 | 71.8 | 67.7 | 85.1 |

TABLE 5-continued

The dose response experiment for J76 in the summer -92. Percentage of diseased sprouts with seed inoculated with *F. culmorum*, and healthy seed. Abbreviations as in FIG. 2.

| | days from emergence | | | |
|---|---|---|---|---|
| treatment | 10 | 17 | 30 | 44 |
| B | 8.4 | 50.4 | 58.3 | 73.6 |
| J76-0 | 14.3 | 48.0 | 69.9 | 73.8 |

Field Trials with J76 Spore Suspension in the Summer -93

The trials were carried out in Jokioinen, Mietoinen and Pälkäne. In the trials six seed samples were used:

'Luja' wheat, naturally infected by the fungus *F. culmorum*

'Luja' wheat, artificially inoculated with the fungus *F. culmorum*

'Luja' wheat, healthy

'Laari' wheat, healthy

'Kustaa' barley, naturally infected by various Fusarium fungi and the fungus *Bipolaris sorokiniana*

'Yty' oat, naturally infected by the fungus *F. avenaceum*

Healthy wheat samples were sown only in Jokioinen, for the other four seed samples trials were carried out in each three test locations. For the trials 10 m² plots were sown with six replications per treatment.

The seed treatments were the same for each of the seed samples:

K=untreated control

B=chemical control, Baytan I dressing

J76S=J76 spore suspension from a plate culture ($8.4 \times 10^9$ cfu/kg seeds)

In Table 6 the intensity of the disease damages is given separately for each treatment and seed sample. The yield results are summarized in Table 7.

TABLE 6

Field trial with J76 spore suspension, -93. Percentage of severely diseased sprouts.

| | BARLEY | OAT | NAT. INF. WHEAT | ARTIF. INOCUL. WHEAT | HEALTHY 'LUJA' | HEALTHY 'LAARI' |
|---|---|---|---|---|---|---|
| JOKIOINEN | | | | | | |
| K | 6.0 | 10.1 | 7.4 | 34.2 | 20.6 | 5.7 |
| B | 0.9 | 2.0 | 2.1 | 1.0 | 1.4 | 0.7 |
| J76S | 0.9 | 1.4 | 0.7 | 1.0 | 3.3 | 5.7 |
| MIETOINEN | | | | | | |
| K | 12.8 | 3.5 | 20.4 | 72.0 | | |
| B | 1.3 | 0.6 | 5.7 | 6.6 | | |
| J76S | 5.4 | 0 | 7.1 | 7.3 | | |
| PÄLKÄNE | | | | | | |
| K | 9.6 | 7.4 | 10.9 | 26.9 | | |
| B | 2.5 | 3.3 | 2.1 | 0.6 | | |
| J76S | 2.4 | 3.6 | 2.3 | 0 | | |

TABLE 7

Yield results from field trials of J76 spore suspension -93. (kg/ha)

| | BARLEY | OAT | NAT. INF. WHEAT | ARTIF. INOCUL. WHEAT | HEALTHY 'LUJA' | HEALTHY 'LAARI' |
|---|---|---|---|---|---|---|
| JOKIOINEN | | | | | | |
| K | 7460 | 6650 | 6060 | 2950 | 6100 | 6360 |
| B | 7500 | 6790 | 5870 | 5690 | 5940 | 6060 |
| J76S | 7840 | 6650 | 6050 | 6040 | 6150 | 6570 |
| MIETOINEN | | | | | | |
| K | 5900 | 5780 | 4920 | 3890 | | |
| B | 6070 | 5200 | 4910 | 4990 | | |
| J76S | 6120 | 5440 | 4670 | 4810 | | |
| PÄLKÄNE | | | | | | |
| K | 4670 | 5560 | 3630 | 2950 | | |
| B | 4550 | 5200 | 4190 | 4000 | | |
| J76S | 4710 | 5430 | 3710 | 3650 | | |

Testing of J76 Against Bunt of Wheat and Foot Rot of Barley

In the summer -93, J76 was included in a field trial, where nine chemical fungicides used for dressing of cereal seeds were tested against bunt of wheat (caused by *Tilletia caries*). J76 was applied as conidial suspensions and the chemicals according to their instructions of use. 0.1 m² plots and five replications were used. (Table 8).

TABLE 8

The effect of the dressing treatments in the bunt of wheat trial.

| TREATMENT | CONTROL EFFICACY (%) (= decrease in the amount of infected ears) |
|---|---|
| Täyssato S liquid | 78 |
| Baytan WS | 100 |
| Beret 050 | 100 |
| Fungazil C | 100 |
| Panoctine 35 | 100 |
| Raxil I powder | 100 |
| Raxil I liquid | 100 |
| Prelude LS | 100 |
| Vitavax 200 FF | 100 |
| J76 | 85 |

In Baytan the active ingredient is triadimenol. Baytan I is a mixture which includes triadimenol and imazalil. Täyssato S comprises carboxin and imazalil. The active ingredient in Panoctine is guazatine.

The treatment of the seeds with J76 spores was also included in a field trial, in which chemical control agents were tested against foot rot (*Bipolaris sorokiniana*) of barley. In the trial 10 m² plots and four replications were used. No differences were found in emerging between different treatments. J76 reduced clearly the symptoms (Table 9), although the pathogen is very much different as compared to the Fusarium fungi against which it is selected.

TABLE 9

The effect of the dressing treatments against the foot rot of barley.

| TREATMENT | CONTROL EFFICACY (%) (= decrease in the amount of diseased sprouts) |
|---|---|
| Prelude LS | 85 |
| Dividend 37.5 (400 ml) | 84 |
| Dividend 37.5 (200 ml) | 81 |
| Baytan I | 81 |
| Beret Special (400 ml) | 74 |
| Raxil I powder | 70 |
| Täyssato S liquid | 66 |
| Panoctine Plus | 66 |
| Fungazil C | 66 |
| Beret Special (200 ml) | 65 |
| Raxil I liquid | 64 |
| Beret FS 050 | 49 |
| PNL 210 | 39 |
| J76 | 69 |

(B) Formulations Prepared From the Fungal Strains, and Their Effect in Field Trials The powder formulations from the J76 fungal strain was prepared as follows:

Formulation 1

The cultivation was carried out in 1 l erlenmeyer bottle having 0.5 l of nutrient medium, which included sucrose 4 g/l, yeast extract 4 g/l and malt extract 10 g/l. pH was adjusted before sterilization in autoclave to 6.0. As an inoculum an agar pellet including spores was used which had been stored at −80° C. (Potato dextrose agar medium). The speed of revolution of the shaker was 150 rpm, growth temperature was the room temperature (22° C.) and cultivation time 7 to 12 days. The cells were separated by filtering on filter paper. To the cell mass silica, milk powder and CMC (carboxymethylcellulose) were mixed as follows:

| | |
|---|---|
| cells | 20%, |
| silica | 55%, |
| milk powder | 15%, |
| CMC (water soln 7%) | 10%. |

The mixture was dried at room temperature on open petri dishes in sterile air for 2 days. The thickness of the layer was 1–2 cm. The dried mixture was ground to powder. The viability of the formulation was 107 cfu/g. (cfu=colony forming units).

cfu (colony forming units) is a unit which is used in the viability determination of microbes. The diluted microbe suspension is spread on agar plates and colonies are counted after a few days. When the dilution is known, the amount of colonies or the amount of microbial cells in the original sample can be counted.

Formulation 2

Cells were cultivated similarly as for Formulation 1, whereafter silica, milk powder, CMC and ascorbic acid were mixed with the cell mass as follows:

| | |
|---|---|
| cells | 60%, |
| silica | 20%, |
| milk powder | 14%, |
| CMC (7%) | 3%, |
| ascorbic acid | 3%. |

The mixture was dried in the same way as Formulation 1 and ground to powder. Viability $10^7$ cfu/g.

Formulation 3

Cells were cultivated similarly as for Formulation 1, whereafter sucrose and starch were mixed with the cell mass as follows:

| | |
|---|---|
| cells | 20% |
| sucrose | 25% |
| starch | 55%. |

The mixture was dried in the same way as Formulation 1 and ground to powder. Viability $10^7$ cfu/g.

Formulation 4

J76 strain was cultivated directly on a solid medium including silica carrier. For the nutrient broth 8% malt extract (Maltax MP10, Lahden Polttimo) was used. 120 g of nutrient broth was mixed in a beaker with 50 grams of silica powder and autoclaved for 20 min at 120° C. The cooled medium was inoculated with 10 grams of J76 spore suspension, which was obtained by scraping the spores from a PDA plate into sterile water. The medium was incubated for 20 days at 16° C., whereafter it was dried at room temperature for 2 days. The viability of the dried preparation was $10^7$ cfu/g.

The rest of the strains of the invention can be formulated similarly.

The Effect of the Powder Formulations in Field Trials

In the following the trials carried out by the Institute of Plant Protection at the Agricultural Research Centre of Finland in the summer -93 with the powder formulation of strain J76 are described. The trials were carried out in MTT (Agricultural Research Centre) in Jokioinen, Mietoinen and Pälkäne. In the trials six seed samples were used:

'Luja' wheat, naturally infected by the fungus *F. culmorum*

'Luja' wheat, artificially inoculated with the fungus *F. culmorum*

'Luja' wheat, healthy

'Laari' wheat, healthy

'Kustaa' barley, naturally infected by various Fusarium fungi and the fungus *Bipolaris sorokiniana*

'Yty' oat, naturally infected by the fungus *F. avenaceum*

Healthy wheat samples were sown only in Jokioinen, for the other four seed samples trials were carried out in each three test places. For the trials 10 m² plots were sown with six replications per treatment.

The seed treatments were the same for each of the seed samples:

K=untreated control

B=chemical control, Baytan I dressing

J76PK=J76 powder as dry dressing (8.4×$10^6$ cfu/kg=the greatest amount taken up by the seeds)

J76PN=J76 powder as liquid dressing (8.4×$10^8$ cfu/kg)

In Table 10 the intensity of the disease damages is given separately for each treatment and seed sample. The yield results are summarized in Table 11.

TABLE 10

Field trials with J76 powder in -93. Percentage of severely diseased sprouts.

| | BARLEY | OAT | NAT. INF. WHEAT | ARTIF. INOCUL. WHEAT | HEALTHY 'LUJA' | HEALTHY 'LAARI' |
|---|---|---|---|---|---|---|
| JOKIOINEN | | | | | | |
| K | 6.0 | 10.1 | 7.4 | 34.2 | 20.6 | 5.7 |
| B | 0.9 | 2.0 | 2.1 | 1.0 | 1.4 | 0.7 |
| J76PK | 2.2 | 1.5 | 2.7 | 7.0 | 6.2 | 2.8 |
| J76PN | 1.2 | 1.9 | 3.9 | 1.3 | 5.7 | 4.6 |
| MIETOINEN | | | | | | |
| K | 12.8 | 3.5 | 20.4 | 72.0 | | |
| B | 1.3 | 0.6 | 5.7 | 6.6 | | |
| J76PK | 10.1 | 0 | 17.2 | 42.5 | | |
| J76PN | 9.1 | 0.3 | 13.7 | 14.3 | | |
| PÄLKÄNE | | | | | | |
| K | 9.6 | 7.4 | 10.9 | 26.9 | | |
| B | 2.5 | 3.3 | 2.1 | 0.6 | | |
| J76PK | 5.3 | 2.6 | 4.8 | 6.1 | | |
| J76PN | 3.9 | 3.8 | 3.9 | 2.7 | | |

TABLE 11

The yield results of the field trials of J76 powder in -93.

| | BARLEY | OAT | NAT. INF. WHEAT | ARTIF. INOCUL. WHEAT | HEALTHY 'LUJA' | HEALTHY 'LAARI' |
|---|---|---|---|---|---|---|
| JOKIOINEN | | | | | | |
| K | 7460 | 6650 | 6060 | 2950 | 6100 | 6360 |
| B | 7500 | 6790 | 5870 | 5690 | 5940 | 6060 |
| J76PK | 7610 | 6940 | 6060 | 5140 | 6400 | 6320 |
| J76PN | 7610 | 6970 | 6040 | 6020 | 6000 | 6400 |
| MIETOINEN | | | | | | |
| K | 5900 | 5780 | 4920 | 3890 | | |
| B | 6070 | 5200 | 4910 | 4990 | | |
| J76PK | 6000 | 5670 | 4770 | 4620 | | |
| J76PN | 6110 | 5760 | 4790 | 4950 | | |
| PÄLKÄNE | | | | | | |
| K | 4670 | 5560 | 3630 | 2950 | | |
| B | 4550 | 5200 | 4190 | 4000 | | |
| J76PK | 4730 | 5560 | 3600 | 3390 | | |
| J76PN | 4870 | 5470 | 3660 | 3760 | | |

In addition, the control effect of different formulations prepared from J76 strain against various fungi were tested in the year -93. The results of these experiments are given in Tables 12 to 18.

TABLE 12

The control effect of J76 in sand soil inoculated by the fungus Gaeumannomyces on Polkka wheat. Pot test, sheltered.

| Treatment | Emergence % | Percentage of fully healthy | Disease index (0–3) | Fresh weight g/replicat. | g/ sprout |
|---|---|---|---|---|---|
| Disease control (not treated with J76) | 78.7 | 65.3 | 0.76 | 5.8 | 0.28 |
| J76 KF dry dressing 8 g/kg | 81.3 | 76.0 | 0.55 | 10.1 | 0.46 |
| J76 liquid dressing $10^6$ cfu/ml | 90.7 | 81.3 | 0.31 | 10.4 | 0.43 |

KF = solid phase preparation (Formulation 4)
Disease index:
0 healthy
1 slightly diseased
2 strongly diseased
3 unemerged

TABLE 13

Control effect of J76 preparations against the fungus *Fusarium culmorum* on Polkka wheat. Pot test, peat as substrate. KF = grown at solid phase (Formulation 4), R = shake cultivation in liquid (Formulation 1), M = microbe as such from agar culture.

| Treatment | Emergence percentage | Percentage of fully healthy | Disease index (0–3) | Fresh weight g/replicat. |
|---|---|---|---|---|
| Healthy | 91 | 84 | 0.37 | 16.2 |
| Disease control | 30 | 5 | 2.54 | 4.5 |
| J76 KF 40/93I liquid dressing $10^6$ cfu/ml | 72 | 44 | 1.17 | 14.0 |
| J76 R 10/2 C liquid dressing $10^6$ cfu/ml | 71 | 49 | 1.21 | 13.0 |
| J76 M $10^6$ cfu/ml | 76 | 58 | 0.99 | 14.8 |

Disease index:
0   healthy
1   slightly diseased
2   strongly diseased
3   unemergeded

TABLE 14

The effect of J76 against the fungus Pythium on cucumber. Results as mean values of three pot tests (pH 6.2, pH 6.9 and pH 7.4).

| Treatment | Percentage of living seedlings | Disease index (0–2) | Fresh weight g/replication |
|---|---|---|---|
| Healthy | 98 | 0.04 | 12.1 |
| Disease control | 47 | 0.63 | 5.4 |
| J76 liquid dressing $10^6$ cfu/ml | 58 | 0.52 | 6.9 |

Disease index:
0   healthy
1   dead
2   unemerged

TABLE 15

The control effect of J76 fungal strain on cauliflower in sand soil contaminated by the fungus *Rhizoctonia solani*. Pot test in greenhouse.

| Treatment | Percentage of emergence | Percentage of fully healthy | Fresh weight g/replication | g/sprout |
|---|---|---|---|---|
| Untreated | 92.7 | 52.0 | 21.7 | 0.79 |
| J76 liquid dressing $10^7$ cfu/ml | 94.7 | 72.0 | 24.1 | 0.84 |

TABLE 16

The control effect of J76 fungal strain on 'Kustaa' barley in sand soil inoculated by the fungus *Fusarium nivale*. Pot test outdoors, sheltered.

| Treatment | Emergence percentage | Percentage of fully healthy | Disease index (0–3) | Fresh weight g/replication |
|---|---|---|---|---|
| Healthy | 93.3 | 37.3 | 0.91 | 8.9 |
| Disease control | 73.3 | 29.3 | 1.43 | 7.8 |
| J76 KF liquid dressing $10^6$ cfu/ml | 80.0 | 52.0 | 0.91 | 9.7 |
| J76 liquid dressing $10^6$ cfu/ml | 81.3 | 52.0 | 0.93 | 10.3 |

Disease index:
0  healthy
1  slightly diseased
2  strongly diseased
3  unemerged

TABLE 17

The control effect of J76 fungal strain against the fungus *Alternaria brassicicola* cauliflower. Results are mean values of experiments at three different temperatures (15° C., 20° C. ja 25° C.).

| Treatment | Percentage of emergence | Disease index (0–3) | Fresh weight g/replication |
|---|---|---|---|
| Healthy | 96 | 0.17 | 33.2 |
| Disease control | 50 | 2.01 | 21.8 |
| J76 liquid dressing $10^6$ cfu/ml | 96 | 0.22 | 35.4 |

Disease index:
0  healthy
1  slightly diseased
2  strongly diseased
3  dead or unemerged The results of the experiments on the control effect of the five Nectria pityrodes strains of the invention (J76, J1431, J1432, MOS1 and ROS2) on Fusarium culmorum on wheat are represented in Table 18. The results are given as mean values of two experiments, in one of which peat was used as substrate and in the other field soil.

TABLE 18

The control effect of five *Nectria pityrodes* strains (J76, J1431, J1432, MOS1 and ROS2) against the fungus *Fusarium culmorum* on wheat. The results are given as mean values of two pot tests (peat and field soil).

| Treatment | Percentage of fully healthy | Disease index (0–3) | Fresh weight (g/replicat.) |
|---|---|---|---|
| Disease control | 23 | 2.06 | 3.0 |
| J76 liquid dressing $10^7$ cfu/ml | 73 | 0.66 | 8.0 |
| J1431 liquid dressing $10^7$ cfu/ml | 80 | 0.51 | 8.5 |
| J1432 liquid dressing $10^7$ cfu/ml | 72 | 0.78 | 8.0 |
| MOS1 liquid dressing $10^7$ cfu/ml | 76 | 0.66 | 8.8 |
| ROS2 liquid dressing $10^7$ cfu/ml | 76 | 0.66 | 8.3 |

Disease index:
0  healthy
1  slightly diseased
2  strongly diseased
3  unemerged (C) Mode of Action by J76

Preliminary observations of the ways by which J76 acts as an antagonist of other fungi, have been made by microscope and in some laboratory tests.

As the interactions of the hyphae of J76 and the fungus *F. culmorum* are observed in a microscope, the first distinct reactions can be found to be very fast. At the points of the contact of the mycelia the cells of the Fusarium hyphae begin to decompose noticeably about one hour after the contact. First the cell walls loose their form, then the cells are emptied and at last also the cell walls decompose totally. From the points of contact the decomposition of Fusarium hyphae spreads slowly forward. When J76 and *F. culmorum* have been growing mixed for a few days, hyphae of the fungus Fusarium cannot be found any more. Also its spores (both conidia and chlamydospores) decompose by the effect of J76, but slower than the hyphae. Usually the J76 hyphae fold loosely around the Fusarium spores before their decomposition. There are no observations according to which J76 would actually penetrate in the Fusarium hyphae.

On the basis of microscope observations it can be concluded that J76 probably secretes biologically active substances to its environment. By nature they can be like enzymes or antibiotics. Their production can well be also the main mode of action by J76 because it has not been found to directly parasitize other fungi, and as it is growing slowly it obviously cannot very effectively compete about nutrients. Hints of production of metabolites effecting the growth of other fungi have been obtained also in a cellophane test.

When J76 and *F. culmorum* grow side by side on a very thin growth substrate, an inhibition zone is formed in which the growth of Fusarium ceases. On a substrate of normal thickness this cannot be found. This is probably due to the small concentrations of the substances diffused into the substrate. Volatile substances secreted by J76 have also found to have weak growth controlling effect on *F. culmorum*.

Cellophane test: On the growth substrate a cellophane film was set and the strain J76 was cultivated on this film. After cultivation of 10 days the film and with it J76 was removed. The substances secreted by J76 and transported through the film remained in the substrate. As a control plates were used which had mere cellophane film without J76. The results of the cellophane test are given in Table 19.

TABLE 19

The effect of metabolites produced by the fungus J76 on growth of *F. culmorum* in the cellophane test, growth rate mm/day

| J76     | 2.5 |
|---------|-----|
| Control | 6.2 |

(D) Performance of the Screening Method and Evaluation of the Results

SAND TESTS

Sowing Substrate

As sowing substrate sand was used, grain size 0.2–0.7 mm (Kauniston Sora Oy, Loimaa). The sand was wetted by mixing to 4 parts of sand 1 part of water. From a serial pot plate (Vefi-VP 96) a plate of 5×7 pots (a 50 ml) was cut which was put in a plastic box. The pots were filled with wetted sand, so that 1–1.5 cm of their upper edge was left empty. To each pot three seeds of 'Luja' spring wheat was sown.

Treatments

*Fusarium culmorum* infection: *F. culmorum* was grown on PDA plates at room temperature for about 1 month (until it fully sporulated). The mycelia with the spores were separated from the plate and mixed with distilled water by Ultra-Turrax homogenizer. The amount of the spores was adjusted to $10^6$ spores/ml. The solution was freezed as 30 ml portions in Minigrip bags to $-20°$ C. For the test the frozen solutions were thawed and remixed. The solution was used as such (basic solution) and as $10^{-2}$ dilution. Pathogenicity of the Fusarium strains was maintained by circulating them through plants (wheat seeds were inoculated by Fusarium suspension and the pathogen was reisolated from diseased sprouts).

Antagonist suspension: A PDA pellet taken from deep-freezer including the antagonist was divided into three parts and was set to grow on three PDA plates. The plates were incubated at room temperature (in dark) for about three weeks. The basic solution of the antagonist suspension was prepared by scraping two antagonist plates to 50 ml of distilled water. It was mixed with Ultra-Turrax homogenizer. From the basic solution the dilutions of $10^{-1}$ and $10^{-3}$ were made.

Seed treatments: 1 ml of *F. culmorum* suspension was first pipetted on the seeds sown to the serial pot plate, and on it 1 ml of antagonist suspension. 15 seeds in five 50 ml pots were treated with all six combinations of spore densities of suspensions (two dilutions of *F. culmorum* suspensions× three dilutions of antagonist suspensions).

Control treatments: Each pot plate used for testing of one fungus had additionally 15 seeds in five pots, which were treated only with the basic solution of the fungus tested.

In sand tests 15 to 30 fungal strains were tested at the same time. Each day the tests were begun also one separate pot plate was sown, with the help of which the health of the seeds as well as the pathogenity of *F. culmorum* inoculum to cause disease was checked. Three control treatmets sown on a separate plate were: uninoculated (water only), inoculation with *F. culmorum* basic solution and inoculation with a dilution of *F. culmorum* basic solution ($10^{-2}$). For each of these three treatments 30 seeds were sown in 10 pots.

Growth conditions: After pipetting of fungal suspensions the seeds were covered with moistened sand. The boxes with the pot plates were wrapped in transparent plastic and were transferred to a growth chamber ($10°–15°$ C., 14 h light period).

Observations

After growing the seedlings for 16 to 18 days, they were washed clean under running tap water, and observations on the disease symptoms in them were made. Sprouts in which root or coleoptile cells had not turned dark, and unemerged seeds which had remained hard were considered healthy. Sprouts which had distinct symptoms, and unemerged seeds which had softened, were considered diseased.

The control treatment plants were examined first. If from water treated seeds only healthy plants had developed, and with both pathogen treatments distinct disease symptoms were obtained, the test was accepted and it was decided to make observations of plants treated with fungal strains to be tested.

In the sand test the grade given to each isolated fungal strain was determined of the number of plants treated with it and considered to be diseased. If the emergence of plants treated with the fungus to be tested only was distinctly reduced compared to healthy control, or if other disease symptoms were found, the fungus was found to be unfit to further tests. If damages were not found, each of the six combinations of spore densities of the pathogen and spore densities of the fungus to be tested were separately graded on the scale:

0=all 15 plants healthy

1=not more than 2 damaged plants

2=3–5 damaged plants

3=6–9 damaged plants

4=10–13 damaged plants

5=not more than one healthy plant

On the basis of six above mentioned individual grades those of the tested fungal strains were selected which were taken to the next test step, i.e. the peat tests. To continuation those strains were accepted which obtained at least three times grades 0 and 1. If the fungus did not obtain any grade 0, it was accepted to continuation if it obtained at least four times grade 1.

PEAT TESTS

Growth Substrate

As growth substrate steamed, fertilized and limed peat was used. Until the autumn 1992 unsifted crude peat from Torronsuo, thereafter already sifted crude peat from Eurajoki was used. (Fertilization: 800 g of dolomite lime and 100 grams of peat Y-lannos/100 l of peat (Y-lannos=trade mark of a Finnish universal fertilizer). Moistened peat was shaped into plastic boxes (28.5×49.5×9.4 cm, Weibulls Robusta "Mammut"-box, Muoviyhtymä Oy) as about 5 cm layer. There was a plastic film on the bottom of the box.

Treatments

T=healthy, non-inoculated seed, 'Luja' spring wheat. Watered with distilled water.

F=*F. culmorum* inoculated seed. The seeds were soaked in *F. culmorum* basic solution (the solution was used in surplus) including about $10^6$ spores/ml (Fusarium cultivation, cf. the sand test). After the treatment the seed were let to dry overnight spread on paper.

F0=*F. culmorum* inoculation as in F-treatment. When the seeds had dried, they were wetted with the basic solution of the antagonist. The basic solution was made by scraping the mycelium and the spores from one antagonist plate into 25 ml of distilled water. The treatment was carried out by shaking the seeds and the antagonist solution in a small plastic bottle. After the treatment the seeds were dried on paper.

F2=*F. culmorum* inoculation as in F-treatment. Antagonist treatment as in F0-treatment, with $10^{-2}$ dilution of the antagonist basic solution.

To the peat 10 rows were sown, 30 seeds/row. The sowing sequence was as follows: protective row, F, F0, F2, T, F, F0, F2, T, protective row. After sowing the seeds were covered with peat and the boxes were wetted.

Growth Conditions

The sowings were grown in a greenhouse at a temperature of about 15° C. At a dark season additional light was given with multimetal lamps for 12 hrs/day. When needed, the sowings were wetted with water. Cultivation time was 18 days.

Grading

The sprouts were washed and observations were made from their disease symptoms as was done after the sand test. On the basis of observations made from the T- and F-treatments it was decided if the result of the test was accepted. The healthy control (T) was not allowed to have more than 12 diseased plants alltogether (out of 60 seeds sown) and the pathogen control (F) had to have at least 52 diseased plants (out of 60 seeds). A tested fungal strain was accepted to the next test phase (field soil trials) if from the seeds treated with one of the two solution concentrations (a 60 seeds) not more than 19 diseased plants were developed.

FIELD SOIL TESTS

Sowing substrate

The soil used (sandy clay) was brought from the field trial area at Jokioinen. The soil was either grounded by hand or (in the winter 1992–1993) through a 1×1 cm table screen. 1.5 l plastic pots (φ14 cm) were filled so that 3–4 cm from the upper edge was left empty. On the bottom of the pot there was a filter paper.

Treatments

1. Healthy seed. Wetted with mere distilled water.

2. Fusarium control. The seeds were wetted with the Fusarium inoculant (preparation, see the sand tests) which had about $10^6$ spores/ml, the solution was used in surplus.

3. Inoculation as in Fusarium control. When the seeds had dried, they were treated with the antagonist suspension which was prepared by mixing the mycelium and spores of one plate to 25 ml of distilled water. The treatment was carried out in a plastic bottle, to which 130 seeds (120–150 seeds) were put, and 1 ml (or 1.5 ml) of antagonist suspension.

4. Fungicide control. Inoculation as in Fusarium control. When the seeds had dried they were treated with 2 g of Baytan I dressing powder per one kg of seeds. Earlier Ceresan and Täyssato S treatments were also used.

The treated seeds were sown into pots, 36 seeds/pot, three replications/treatment. The sowings were covered with field soil. Growth conditions as in the peat test. Cultivation time about four weeks.

Examination and Grading

The sprouts were washed and their disease rate was evaluated:

0=fully healthy
1=light Fusarium damage
2=moderate-strong disease damages
3=sprouts browned all over—dead

The Effectivity of the Greenhouse Tests

In the summer -93 in one broad field trial the effectivity of the selection method of the invention was tested. In the test it was examined if the correct ones of the isolated fungal strains-had been taken to further tests during the selection test series between October 1991 and February 1993. To seed treatments arbitrarily 60 of those strains were chosen which had been abandoned in sand tests and which had not shown to be pathogenic to wheat. Of the strains being discarded in the peat tests 92 were allotted to the test. All 58 fungi selected to the soil tests were also taken to the test. 43 of these had been discarded in the soil test and 15 had been selected on the basis of it to the field trials.

In addition to the above mentioned 210 treatments the test included also 6 control treatments: Untreated (K), Baytan I dressing (B) and four fungal strains studied mostly in earlier tests, a.o. J76.

In the test 'Luja' wheat naturally infected by the fungus *F. culmorum* was used. As the observation unit was a 1.4 m long sprout row, for sowing of which 5.5 g of seeds was used. Six replications was sown for all 216 treatments. The randomizing of the test was made according to cubic lattice experimental design. In this way the error variation attributable to soil factors was reduced. After about five weeks from the sowing the sprouts were dug out of the soil, they were counted and their disease symptoms were studied.

The results of the test are illustrated by four histograms in FIGS. 3*a* to 3*d*. Between the isolates discarded in the peat test and non-pathogenic isolates discarded in the sand test no difference can be found. The peat test has obviously worked pretty well. The strains taken therefrom to further tests were on the average clearly better than the fungi discarded in it.

Alltogether in the sand and peat tests relatively few fungi were abandoned, which should not have been discarded. On the other hand on the basis of the soil test a substantial amount of the very best isolates were abandoned, but from those taken to the field trials only two of fifteen had defective effect in natural conditions.

From the results one can conclude that on the basis of the sand and peat tests one can reliably select the best antagonists to further studies, but in field soil tests even good antagonist candidates can be discarded.

The Testing of the Fungal Strain J1431 in Selection Tests

Of the fungal strains of the invention J1431 was tested in all three selection experiments made in greenhouse.

In the sand test J1431 obtained the grades 0, 0, 1, 1, 1 and 2, and was taken to further tests.

In the peat test J1431 obtained the following results:

T: 3 diseased
F: 36 diseased

F0: 3 diseased

F2: 7 diseased

In the field soil test, where J1431 was included, the percentages of diseased sprouts were in different treatments:

| healthy | 66% |
|---|---|
| Fusarium control | 87% |
| Baytan I dressing | 31% |
| J1431 | 19% |

On the basis of the selection tests J1431 was taken to a field trial with 61 other fungal strains in the summer -93. In the test 'Luja' spring wheat artificially inoculated with the spore suspension of the fungus *F. culmorum* was used. The seeds where sown to single row (1.4 m) plots and the test had six replications. After 34 days from sowing the sprouts were dug out of the soil, washed and the observations of their disease symptoms were made. As the amount of healthy sprouts per row meter in different treatments was obtained:

| Fusarium control | 5.9 |
|---|---|
| Baytan I dressing | 56 |
| J76 | 61 |
| J1431 | 65 |
| other tested strains | 30–68. |

The Testing of the J1432 Fungal Strain in Selection Tests

J1432 was tested in all three selection tests made in greenhouse.

In the sand test J1432 obtained the grades 0, 0, 0, 1, 1 and 2 and was taken to further tests.

In the peat test J1432 obtained the following results:

T: 10 diseased

F: 60 diseased

F0: 10 diseased

F2: 37 diseased

In the field soil test, where J1432 was included, the percentages of diseased sprouts in different treatments were:

| healthy | 56% |
|---|---|
| Fusarium control | 98% |
| Baytan I dressing | 18% |
| J1432 | 38% |

On the basis of the results of the field soil test J1432 was left away from the field trials.

Deposited Microorganisms

The following microorganisms were deposited according to the Budapest Treaty at DSM-Deutsche Sammlung von Mikroorganismen und Zellkulturen GmbH, Mascheroder Weg 1 b, D-38124 Braunschweig, Germany

| Microorganism | Deposit number | Deposition date |
|---|---|---|
| Nectria pityrodes Montagne J76 | DSM 7522 | 15 March 1993 |
| Nectria pityrodes Montagne J1431 | DSM 8805 | 10 Dec. 1993 |
| Nectria pityrodes Montagne J1432 | DSM 8806 | 10 Dec. 1993 |
| Nectria pityrodes Montagne MOS1 | DSM 8807 | 10 Dec. 1993 |
| Nectria pityrodes Montagne ROS2 | DSM 8808 | 10 Dec. 1993 |

We claim:

1. A biologically pure culture of the strain *Nectria pityrodes* Montagne DSM 7522.

2. A biologically pure culture of the strain *Nectria pityrodes* Montagne DSM 8805.

3. A biologically pure culture of the strain *Nectria pityrodes* Montagne DSM 8806.

4. A biologically pure culture of the strain *Nectria pityrodes* Montagne DSM 8807.

5. A biologically pure culture of the strain *Nectria pityrodes* Montagne DSM 8808.

6. A method for controlling pests in a plant or seeds, which comprises applying to said plant or seeds a pesticidal effective amount of a pesticide comprising at least one strain of *Nectria pityrodes* selected from the group consisting of DSM 7522, DSM 8805, DSM 8806, DSM 8807 and DSM 8808.

7. A biofungicidal composition, which comprises at least one biologically strain of *Nectria pityrodes* selected from the group consisting of DSM 7522, DSM 8805, DSM 8806, DSM 8807 and DSM 8808, and at least one carrier or additive.

8. A method for inhibiting a fungal infection in a plant, which comprises applying to the plant or seeds thereof a fungicidal effective amount of the biofungicidal composition according to claim 7 or adding a fungicidal effective amount of said biofungicidal composition into a substrate used for growing the plant before or after sowing seeds of the plant.

9. The composition according to claim 7, wherein the carrier is selected from the group consisting of silica, carboxymethylcellulose, sucrose, and starch.

10. A method for inhibiting a fungal infection in a plant, which comprises applying to a plant or seeds thereof a fungicidal effective amount of the biofungicidal composition according to claim 9 adding a fungicidal effective amount of said composition into a substrate used for growing before or after sowing seeds of the plant.

11. The composition according to claim 7 which is produced by a process comprising the steps of growing said strain in an appropriate growth medium to produce a cell mass, separating said cell mass and adding thereto at least one carrier, and drying and powdering the mass obtained.

12. The composition of claim 11 wherein the carrier is selected from the group consisting of silica, carboxymethylcellulose, sucrose, and starch.

13. A method for inhibiting a fungal infection in a plant, which comprises applying to a plant or seeds thereof a fungicidal effective amount of the biofungicidal composition according to claim 11 or adding a fungicidal effective amount of said composition into a substrate used for growing before or after sowing seeds of the plant.

14. The composition according to claim 11, wherein said process further includes the step of introducing at least one additive to the cell mass.

15. The composition according to claim 14, wherein the additive is selected from the group consisting of milk powder, carboxymethylcellulose, sucrose, ascorbic acid, and starch.

16. A method for inhibiting a fungal infection in a plant, which comprises applying to a plant or seeds thereof a fungicidal effective amount of the biofungicidal composition according to claim 14 adding a fungicidal effective amount of said composition into a substrate used for growing the plant before or after sowing seeds of the plant.

17. The composition according to claim 7 which is produced by a process comprising the steps of growing said strain in an appropriate growth medium with a silica carrier to obtain a cell mass, and drying and powdering the mass obtained.

18. A method for inhibiting a fungal infection in a plant, which comprises applying to a plant or seeds thereof a fungicidal effective amount of the biofungicidal composition according to claim 17 or adding a fungicidal effective amount of said composition into a substrate used for growing the plant before or after sowing seeds of the plants.

19. The composition according to claim 17, wherein said process further includes the step of introducing at least one additive to the cell mass.

20. The composition according to claim 19, wherein the additive is selected from the group consisting of milk powder, carboxymethylcellulose, sucrose, ascorbic acid, and starch.

21. The composition according to claim 7, comprising at least one additive.

22. The composition according to claim 21, wherein the additive is selected from the group consisting of milk powder, carboxymethylcellulose, sucrose, ascorbic acid, and starch.

23. A method for inhibiting a fungal infection in a plant, which comprises applying to a plant or seeds thereof a fungicidal effective amount of the biofungicidal composition according to claim 21 or adding a fungicidal effective amount of said composition into a substrate used for growing the plant before or after sowing seeds of the plant.

* * * * *